(12) United States Patent
Noble

(10) Patent No.: US 6,561,193 B1
(45) Date of Patent: May 13, 2003

(54) NASAL GAS DELIVERY APPARATUS AND A NASAL VESTIBULAR AIRWAY

(75) Inventor: James P. Noble, Stuart, FL (US)

(73) Assignee: Linda J. Noble, Stuart, FL (US)

(*) Notice: Subject to any disclaimer, the term of this patent is extended or adjusted under 35 U.S.C. 154(b) by 0 days.

(21) Appl. No.: 09/430,038

(22) Filed: Oct. 29, 1999

Related U.S. Application Data

(60) Provisional application No. 60/106,271, filed on Oct. 30, 1998.

(51) Int. Cl.$^7$ ............................ A61M 15/08; A62B 7/00
(52) U.S. Cl. ............................................ 128/207.18
(58) Field of Search ................ 128/200.22, 204.12, 128/207.13, 207.18, DIG. 26, 912, 202.24

(56) References Cited

U.S. PATENT DOCUMENTS

| | | | | |
|---|---|---|---|---|
| 1,155,608 A | | 10/1915 | Nieschang | |
| 3,915,173 A | * | 10/1975 | Brekke | 128/207.18 |
| 4,465,067 A | * | 8/1984 | Koch et al. | 128/207.18 |
| 4,622,965 A | * | 11/1986 | Teeple | 128/207.14 |
| 4,648,398 A | * | 3/1987 | Agdanowski et al. | 128/207.18 |
| 4,660,555 A | * | 4/1987 | Payton | 128/207.18 |
| 4,676,241 A | * | 6/1987 | Webb et al. | 128/207.14 |
| 4,742,824 A | * | 5/1988 | Payton et al. | 128/207.18 |
| 4,753,233 A | | 6/1988 | Grimes | |
| 4,782,832 A | * | 11/1988 | Trimble et al. | 128/207.18 |
| 4,915,104 A | * | 4/1990 | Marcy | 128/207.18 |
| 4,915,105 A | * | 4/1990 | Lee | 128/205.27 |
| 4,996,983 A | * | 3/1991 | AmRhein | 128/206.11 |
| 5,042,476 A | * | 8/1991 | Smith | 128/207.14 |
| 5,062,420 A | * | 11/1991 | Levine | 128/204.18 |
| 5,113,857 A | * | 5/1992 | Dickerman et al. | 128/207.18 |
| 5,117,818 A | * | 6/1992 | Palfy | 128/204.11 |
| 5,188,101 A | * | 2/1993 | Tumolo | 128/207.18 |
| 5,222,486 A | | 6/1993 | Vaughn | |
| 5,267,556 A | | 12/1993 | Feng | |
| 5,269,296 A | * | 12/1993 | Landis | 128/207.18 |
| 5,284,134 A | * | 2/1994 | Vaughn et al. | 128/200.24 |
| 5,311,863 A | * | 5/1994 | Toppses et al. | 128/207.15 |
| 5,333,608 A | * | 8/1994 | Cummins | 128/207.14 |
| 5,469,864 A | * | 11/1995 | Rosenblatt | 128/849 |
| 5,507,535 A | * | 4/1996 | McKamey et al. | 285/168 |
| 5,524,642 A | * | 6/1996 | Rosenblatt | 128/849 |
| 5,533,506 A | * | 7/1996 | Wood | 128/207.18 |
| 5,535,739 A | * | 7/1996 | Rapoport et al. | 128/204.23 |
| 5,595,174 A | * | 1/1997 | Gwaltney | 128/201.15 |
| 5,775,335 A | | 7/1998 | Seal | |
| 6,076,520 A | * | 6/2000 | Cooper | 128/200.21 |
| 6,119,694 A | * | 9/2000 | Correa et al. | 128/207.13 |

* cited by examiner

Primary Examiner—Weilun Lo
Assistant Examiner—Joseph F. Weiss, Jr.
(74) Attorney, Agent, or Firm—Wenderoth, Lind & Ponack, L.L.P.

(57) ABSTRACT

A gas delivery apparatus includes a nasal airway having a gas passage therein for insertion into the nose, a swivel connected to the nasal airway and tubing connected to the swivel. The swivel has a gas passage therein that communicates with the gas passage with the nasal airway. Further, the tubing has a proximal portion connected to the swivel so as to be in fluid communication with the gas passage of the swivel. The tubing bends so that an angle is formed between the distal portion of the tubing and the proximal portion of the tubing. The nasal airway preferably includes a nasal vestibular portion that is adapted to fit in a nasal vestibule, a connection portion extending from the nasal vestibular portion and the gas passage that extends through the connection portion and through the nasal vestibular portion. The nasal vestibular portion flares outwardly with respect to the connection part.

5 Claims, 4 Drawing Sheets

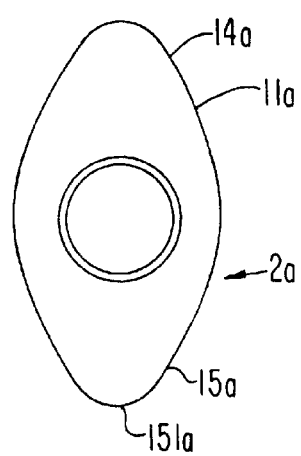
FIG. 5a
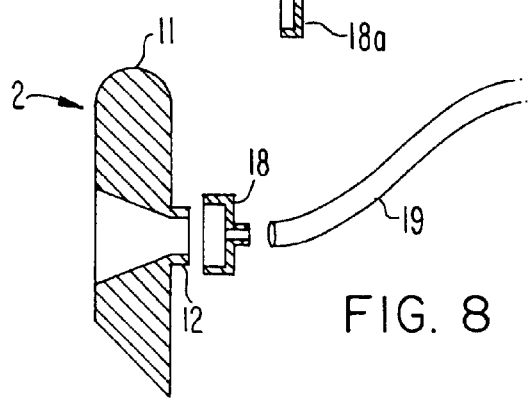
FIG. 8a
FIG. 8
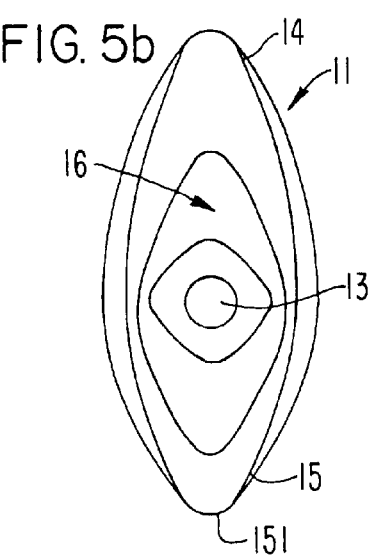
FIG. 5b
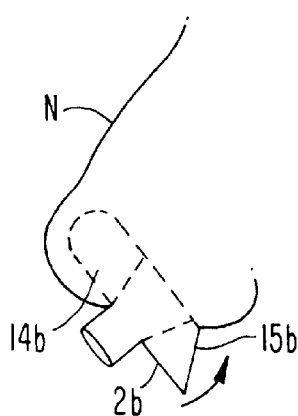
FIG. 6a
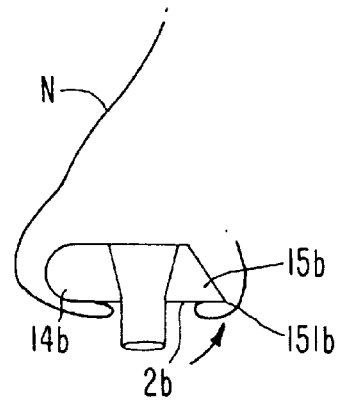
FIG. 6b
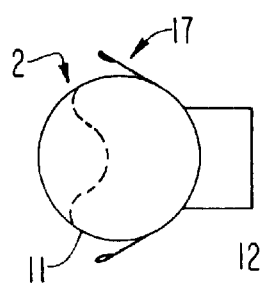
FIG. 7
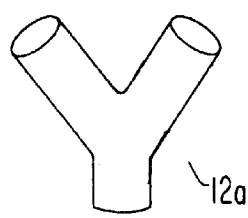
FIG. 9

NASAL GAS DELIVERY APPARATUS AND A NASAL VESTIBULAR AIRWAY

This is a Utility Application claiming priority on Provisional Application 60/106,271, filed Oct. 30, 1998.

BACKGROUND OF THE INVENTION

The present invention relates to anesthetic/gas delivery apparatus for delivering anesthetic to a patient during surgery, and more particularly for delivering anesthetic to a patient during plastic surgery.

In the sequence of events of drug-induced depression of the central nervous system there occurs a level of depression that allows the muscles of the pharynx (e.g. the tongue) to relax causing soft-tissue structures to collapse into and obstruct the airway. This happens at an earlier stage than that at which the muscles of respiration (e g. the diaphragm) cease to function. In other words, the condition known as "obstructive apnea", where the diaphragm is struggling to pull air through an obstruction of the upper airway occurs before the diaphragm, itself, ceases to function ("central apnea"). In this sequential depression of the central nervous system, death occurs from asphyxia before the drug, itself, can produce complete depression of the nervous system.

This condition of obstruction occurs upon the induction of almost every general anesthetic and is a frequent occurrence during the administration of heavy sedation for procedures done nominally under "local anesthesia with sedation. " Under most conditions the treatment is so routine as to be taken for granted by practitioners skilled in airway management. Manual support of the airway, application of a face mask over the mouth and nose and various airway devices are employed, often with supplemental oxygen.

Recent advances in cosmetic surgery, however, have made airway management significantly more challenging and have caused practitioners to accept conditions having a reduced margin of safety for their patients. In particular, LASER procedures on the face are requiring heavier sedation leading more often to respiratory depression and obstruction while, at the same time, the increased fire hazard restricts the use of oxygen.

SUMMARY OF THE INVENTION

Observations of drug-induced respiratory dysfunction and its treatment can be characterized as a Syndrome of Narcogenic Obstructed Respiration (SNOR). The syndrome is characterized by the following features. Firstly, a drug-induced depression of the central nervous system is caused, which secondly leads to an acute and complete upper airway obstruction, and which thirdly can lead to asphyxia and death.

SNOR is preventable by applying positive pressure through the nasopharynx while leaving the oral cavity open to ambient pressure. The pressure differential thus created splints the soft tissues out of the airway with a natural pressure relief valve through the oral cavity. The maximum pressure obtainable is consistently sufficient to relieve the obstruction, but less than the 20 centimeters of water that might send air to the stomach.

This concept is new to the thinking of anesthesia practitioners, who traditionally apply a face mask as a first-line remedy of upper airway obstruction. However, the standard face mask places pressure on the chin and tends to collapse soft-tissue structures of the oropharynx. Additionally, air pressure that is applied through the face mask tends to equalize through the nose and the mouth, and therefore it can be counter-productive to the stenting-up of soft tissue to open the airway. Further, using a face mask usually requires one or two additional maneuvers, for example manual support of the chin, the insertion of an oral airway, etc., in order to remedy the problem.

The treatment of Obstructive Sleep Apnea (OSA), a syndrome defined in the early 1980's, has demonstrated that upper airway obstruction occurring during the sleep of afflicted patients can be relieved by the application of positive pressure through the nose alone. The present inventor has recognized that this can be of significant usefulness in cosmetic surgery practice.

Accordingly, it is an object of the invention to provide an anesthetic delivery apparatus which can provide Continuous Positive Airway Pressure (C-PAP) through the nose in order to prevent an upper airway obstruction.

OSA is similar to SNOR in anatomy and treatment, but differs in that it is not drug-induced, with acutely disastrous consequences, but rather is a chronic condition with long-term ill-effects. SNOR is treated according to the apparatus of the present invention by modified application of C-PAP as used in obstructive sleep apnea.

A gas delivery apparatus according to the present invention includes a nasal airway having a gas passage therein for insertion into the nose. A swivel is connected to the nasal airway, the swivel having a gas passage therein communicating with the gas passage of the nasal airway. Tubing has a proximal portion connected to the swivel so as to be in fluid communication with the gas passage of the swivel. The tubing bends so that an angle is formed between the distal portion of the tubing and the proximal portion of the tubing.

The nasal airway may comprise a rubber naso-pharyngeal airway, or may preferably comprise a nasal vestibular portion that is adapted to fit in a nasal vestibule. The nasal vestibular portion has a connection part that connects the nasal airway to the swivel. The nasal vestibular portion flares outwardly with respect to the connection part, and the gas passage of the nasal airway extends through both the connection part and the nasal vestibular portion.

The nasal vestibular portion comprises a superior pole for engaging the apex of a nasal vestibule. Further, an inferior pole of the nasal vestibular portion is provided to engage an inferior nostril rim of the nasal vestibule. The superior pole is elongate and rounded, and the inferior pole comprises an angled wedged shape. Thus, the superior pole, lodged in the apex of the nasal vestibule, helps to direct the inferior pole with the angled wedge shape against the inner surfaces of the nose to push the surfaces outward, thereby sealing.

The nasal vestibular portion may comprise a flexible material. In this case, a thin flap can be provided around the perimeter of the nasal vestibular portion for providing further sealing with the nasal interior.

A second nasal vestibular portion can be provided to connect with the second nostril of a patient. The second nasal vestibular portion also flares outwardly with respect to the connection part. In this instance, the connection part has one portion in which the gas passage of the connection part is connected with the swivel, and another portion in which the gas passage of the connection part branches into two gas passages communicating with the first and second nasal vestibular portions.

The tubing can include a plurality of swivels to provide for the ability to swivel the tubing not only from side to side, but also from the upper to the lower position with respect to the patient's head. The head strap and/or an ear hook may be connected to the tubing to hold the tubing on the head of the patient.

A nasal plug can also be adapted to close one nostril when only one nasal airway is supplied with gas. The nasal plug may be similar to the nasal airway which comprises a connection part and a nasal vestibular portion, but in this case would have its gas passage blocked, for example by a cap. Alternatively, the cap could include a small opening to receive an oxygen tube to provide oxygen to the nostril.

The tubing may also have vent holes therein. Further, it may be bent so as to form an acute angle between the proximal portion and the distal portion.

BRIEF DESCRIPTION OF THE DRAWINGS

FIG. 5a is a top view of a first embodiment of a nasal airway according to the present invention;

FIG. 5b is a plan view of a second embodiment of a nasal airway according to the present invention;

FIGS. 6a and 6b illustrate how the nasal airways according to the first and second embodiments are inserted into the nostril of a patient;

FIG. 7 is an end view of a modification of the nasal airway of FIG. 5b;

FIG. 8 is a partly cross-sectional view of a modification of a nasal airway according to the present invention;

FIG. 8a is a cross-sectional view of a cap for use with the modification of FIG. 8;

FIG. 9 illustrates a modification of a connecting portion of the nasal airway according to the present invention;

DETAILED DESCRIPTION OF THE PREFERRED EMBODIMENTS

Figure 1:
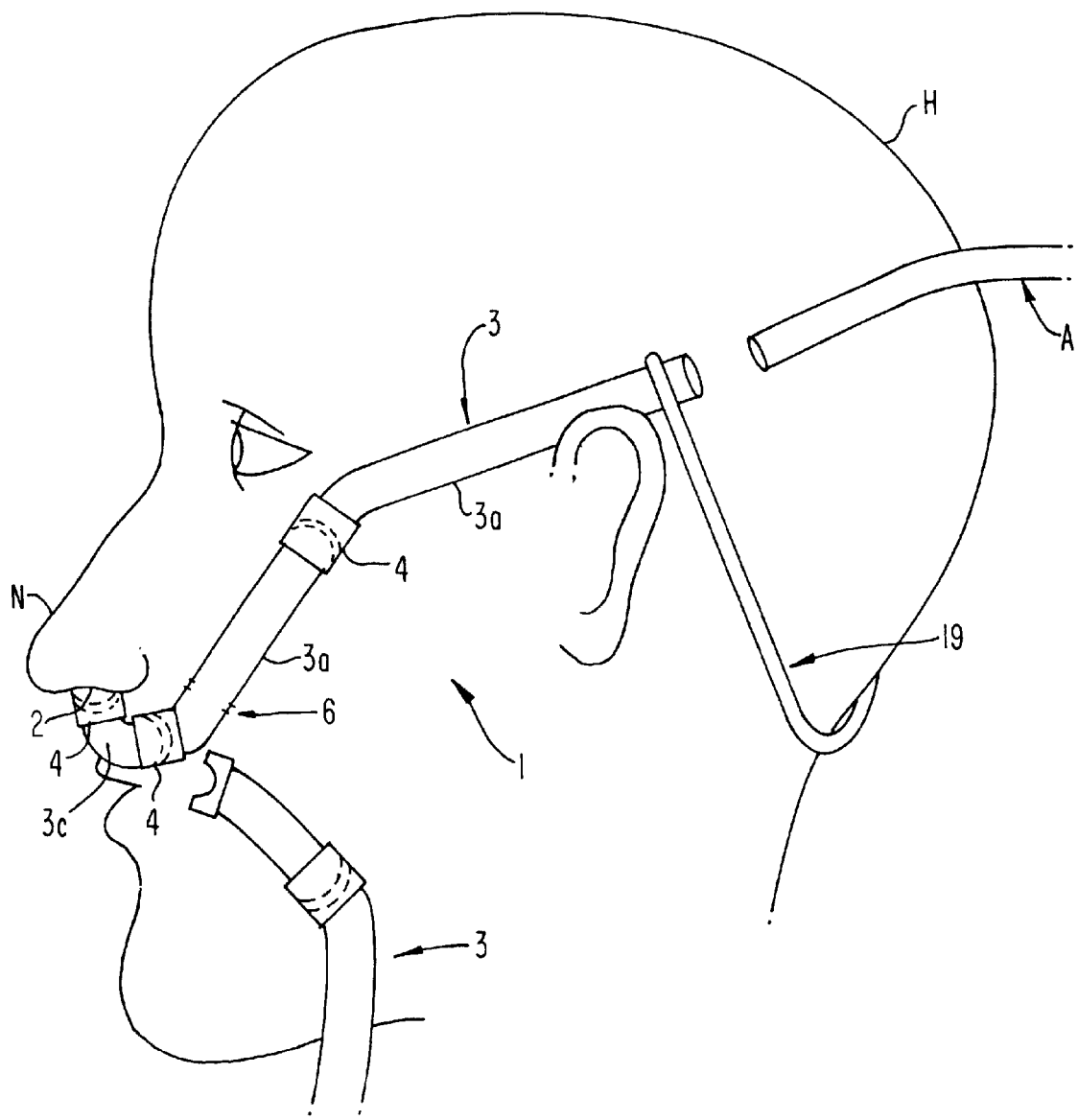
FIG. 1 is an illustration of a gas delivery apparatus according to the present invention as employed upon the head of a patient, showing one alternative position of tubing thereof.

FIG. 1 generally illustrates a first embodiment of a gas delivery apparatus according to the present invention. The gas delivery apparatus is generally designated by reference 1 and includes the main components of a nasal vestibular airway 2, tubing 3 and swivels 4 interconnecting the tubing 3 and the nasal vestibular airway 2. Tubing 3 can include segments which form a 135 degree bend 3a, segments which form a 90 degree bend 3c, or segments which are straight 3b (see FIG. 3).

The tubing 3 illustrated in FIG. 1 is shown as disconnected adjacent to a head strap 19. However, the tubing 3 will obviously be further connected to additional flexible tubing such as schematically illustrated by reference A. This flexible tubing A can be connected to an airflow generator, for example. In accordance with the preferred usage of the present invention, the tubing is used to treat SNOR as described above by the application of C-PAP, or continuous positive airway pressure. Thus, the tubing can be connected to an anesthesia circuit, and/or a C-PAP flow generator. It is noted that the tubing 3 combined with the swivels 4 can also be used to link standard devices such as a naso-pharyngeal airway, LMA, COPA or endotracheal tubes.

According to one advantageous feature of the present invention, the swivels are provided such that anesthetic delivery through the nasal vestibular airway 2 into nose N occupies a small amount of space with respect to the patient, extends out of the nose N, and turns back up and across the head of the patient so as to be out of the way. The combination of tubes forming a substantially 135 degree angle from the direction of the tubes coming out of the nasal vestibular airway 2 to the direction of tube 3a permits this to happen. The first swivel 4 immediately adjacent to the nasal vestibular airway 2 allows the tubing 3 to be pivoted from one side of the head H of the patient to the other side. The swivel 4 between tubings 3a and 3c allows the portions 3a of the tubing to be pivoted from an upper position extending behind the ear shown in the figure, to a lower position also shown in the figure extending below the chin. This is simply schematically shown by the additional presence of the lower tubing reference 3. An additional swivel 4 makes the tubing 3 overall more flexible in being properly positioned adjacent to and around the head of the patient.

Figure 2:
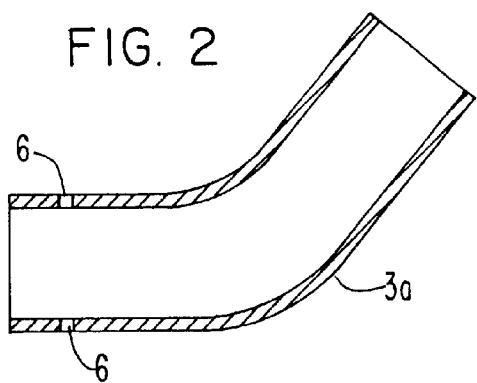
FIG. 2 is cross-sectional view of a 135 degree bend tube for use in the tubing of the gas delivery apparatus according to the present invention.
Figure 4:
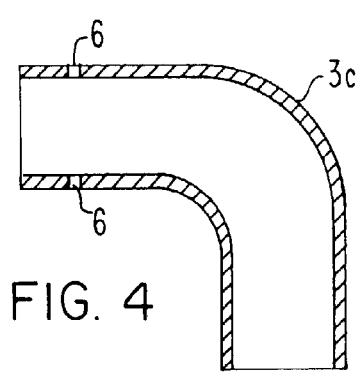
FIG. 4 is a cross-sectional view of a 90 degree bend tube.

FIG. 2 shows a cross-section of tubing 3a, and FIG. 4 shows a cross-section of tubing 3c. The tubing 3 may have optional vent holes 6.

Figure 3A:
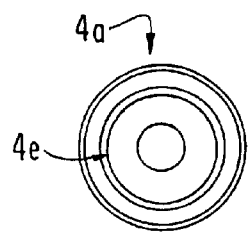
FIG. 3a is a plan view of a first swivel member.
Figure 3B:
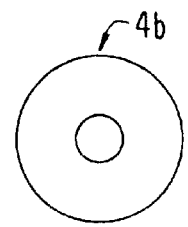
FIG. 3b is a plan view of a second swivel member.
Figure 3:
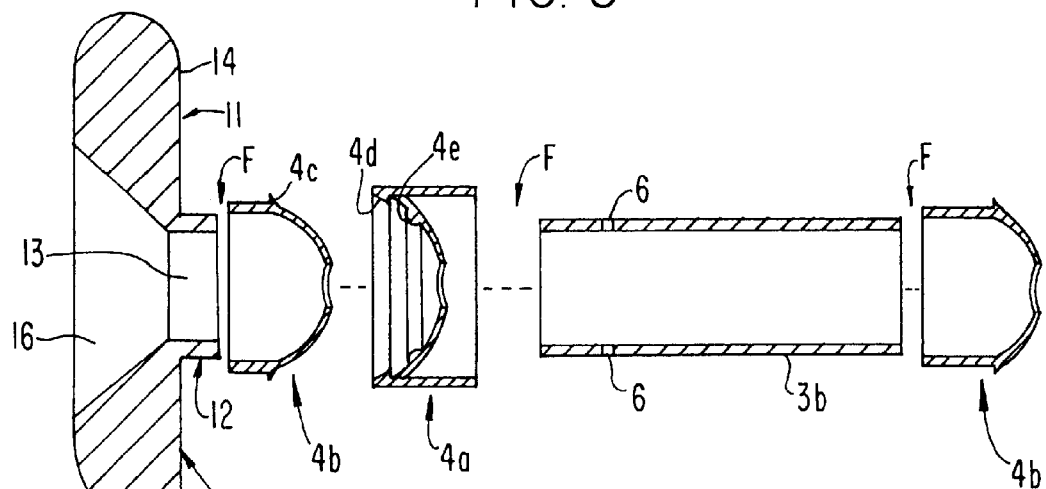
FIG. 3 is an exploded cross-sectional view of a nasal airway, swivel and tube used in the gas delivery apparatus.

Referring now to FIG. 3, in particular, there is shown the nasal vestibular airway 2 according to one embodiment of the present invention. The nasal vestibular airway 2 comprises a nasal vestibular portion 11 and a connection part 12. The connection part 12 is a cylindrical extension from the nasal vestibular portion 11 formed to connect with a swivel 4, as will be explained in more detail below. The nasal vestibular portion can also be seen from the top view illustrated in FIG. 5b. The nasal vestibular portion 11 overall has an oval or football shape designed to fit in the nasal vestibule. A superior pole 14 is elongate and rounded and is designed to fit into the spacious apex of the vestibule of the nose. An inferior pole 15 of the nasal vestibular portion 11 has a 45 degree wedge 151 formed at its lower pole, best seen in FIG. 3. The acute angled outer edge of the inferior pole 15 allows the nasal vestibular airway 2 to grip the narrow inner ridge of the inferior nostril rim. The superior pole 14 generates elasticity in the apex of the vestibule of the nose which will firmly hold the sharp inferior edge 151 of the nasal vestibular airway 2 in the shallow space of the vestibule behind the narrow inferior nostril rim.

An air or gas passage 13 extends through the connecting part 12 in the main nasal vestibular portion 11. In the embodiment of FIG. 3 and FIG. 5b, the passage 13 connects with a conic portion 16. However, as shown by FIG. 5a a nasal vestibular airway 2a can have a superior pole 14a, inferior pole 15a with wedge 151a. A nasal vestibular portion 11a of this embodiment has a passage extending straight therethrough without forming the conic shape of FIG. 5b and FIG. 3.

FIGS. 6a and 6b show a modification of the nasal vestibular airway 2, to the wedge 151. In this embodiment, the wedge 151b is shaped so that a curved or slanted surface is formed toward the sharp 45 degree edge of the wedge 151b. Accordingly, the inferior pole 15b can be angled up into the nose as shown by the arrows in the figures after insertion of the superior pole 14 into the apex of the vestibule of the nose end. This allows for easier insertion of the nasal vestibular airway into the nose N.

Thus, in accordance with FIGS. 6*a* and 6*b*, the superior pole 14*b* is inserted into the nasal vestibule, the nasal vestibular airway 2*b* is rotated over the inferior nostril rim, and the sharp angle of the wedge 151*b* locks the nasal vestibular airway 2*b* in place in the nasal vestibule. Sealing forces of the nasal vestibular airway are against the inner surfaces of the nose to provide an outward force on the inner surfaces of the nose.

Nasal vestibular airway 2 may be made of metal, teflon, silicon or other rubber-like materials. If the flexible material like silicon, for example, is used for the nasal vestibular airway, a thin flap 17 may be incorporated into the perimeter of the nasal vestibular airway 2 in order to provide a better seal. This is illustrated in FIG. 7. The flap 17 is preferably compressible.

Nasal vestibular airway 2 can be adapted to form a plug. For example, while one nasal vestibular airway 2 might be employed in one nostril, the other nostril might be plugged to avoid respiration therethrough. Accordingly, a nasal vestibular airway 2 is illustrated in FIG. 8 that is provided with a cap 18*a* shown in FIG. 8*a*. Alternatively, a cap 18 having a small opening adapted to be connected to oxygen tubing 19 can be provided instead of the cap 18*a*. This would allow a supply of oxygen to one nostril for situations, for example, involving chronic lung disease.

A Y-connector 12*a* is illustrated in FIG. 9. This can be used in place of the connecting part 12 together with the nasal vestibular portion 11, for example. Thus, the bottom single branch of the Y-connector 12*a* may be connected to the tubing 3, for example through a swivel 4, while the upper two branches are connected to respective nasal vestibular portions 11. Alternatively, the upper branches could be adapted to connect to the connecting part 12 of respective nasal vestibular airways 2.

It has been noted that the tubing 3 may include the vent holes 6. The vent holes are provided in the tubing in order to prevent rebreathing in carbon dioxide accumulation in uses outside of the operating room. The tubing itself is preferably fire resistant, but can be made of rubber, or a more fire-retardant material, including teflon, metal or ceramic-impregnated silicon.

Connecting the tubing 3 and the nasal vestibular airway 2 are respective swivels 4. Each swivel includes a male part 4*b* and a female part 4*a* for connection with each other. This type of swivel, which is per se known as a swivel connector, includes a lip 4*c* on the male part 4*b* for engagement with a catch 4*d* on the female part 4*a*. Both the lip 4*c* and the catch 4*d* are annular. A front surface of the male part 4*b* can thus extend into an interiorly extending portion of the female part 4*a* so that the surface of the male part 4*b* engages with an annular rib 4*e*. After connection of the lip behind the catch 4*d* the male part 4*b* can be rotated relative to the female part 4*a* with the front surface of the male part 4*b* riding on the rib 4*e*.

The swivel 4, as well as the nasal vestibular airway 2 and the tubing 3, is preferably made of a plastic material such as teflon. In any case, the material is preferably laser-resistant, non-conductive and fire-retardant but other materials may be suitable depending upon the application. For example, both the swivel and the nasal vestibular airway 2 could be made out of metal. For example, the metal swivel could include a swivel housing that houses a bushing which subsequently houses a tube for connection to the tubing 3 or the nasal vestibular airway 2.

Returning again to the swivel of FIG. 3, the swivel 4 is preferably compression fit with respect to the connecting part 12 of the nasal vestibular airway 2 and the tubing 6. The locations of compression fits of the respective components are illustrated, for example, by reference F in FIG. 3.

Figure 10:
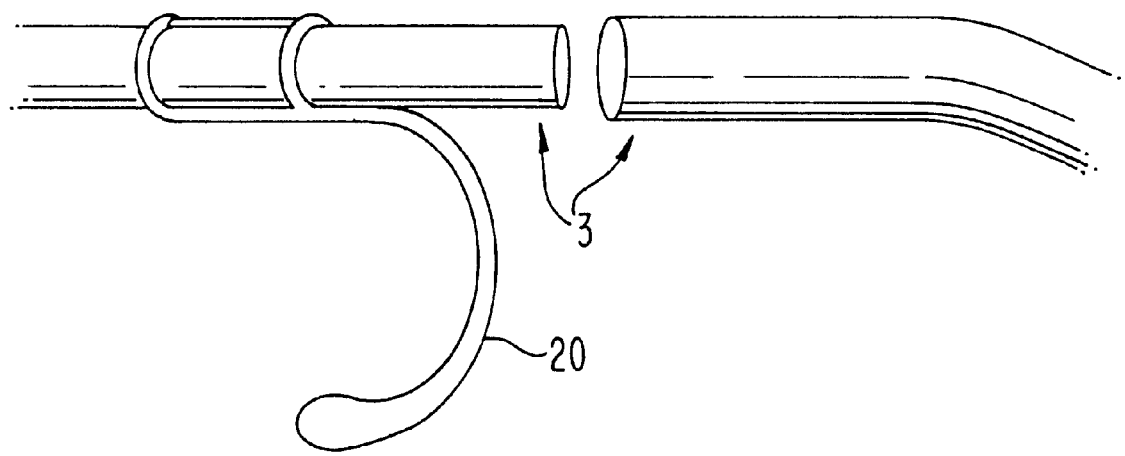
FIG. 10 shows a "glasses" type of ear hook for use with tubing of the gas delivery apparatus according to the present invention.

FIG. 10 illustrates another type of strap for connecting the tubing 3 to the head of the patient. In this figure there is shown a "glasses" type of ear hook for hooking the tubing to the ear of the patient. This could be used in place of the head strap 19 of FIG. 1. The strap 19 of FIG. 1 may be more preferably used in situations with paired nasal vestibular airways 2. Such paired nasal vestibular airways 2 might be used in situations involving the application of continuous positive airway pressure for obstructive sleep apnea, or acute respiratory failure. Accordingly, with the gas delivery apparatus, not only is anesthetic delivery more convenient and easier, particularly in plastic surgery situations, but the apparatus may also be used in a number of other situations.

For example, as noted above, the apparatus according to the present invention may be used in the treatment of OSA for application of C-PAP. Other uses outside of the operating room can be applied to the gas delivery apparatus according to the present invention. For example, by appropriate sizing of the respective components, the gas delivery apparatus according to the present invention could be used in newborn intensive care nurseries to administer continuous positive airway pressure. In intensive care, in the emergency room and in an ambulance, the gas delivery apparatus according to the present invention may allow for more effective respiratory assistance for a spontaneously breathing but severely compromised patient.

Various modifications of the present invention will occur to those of ordinary skill in the art. For example, the tubing section 3 does not necessarily require the specific angles recited above. Different angles may be appropriate depending on the circumstances. Further, the three swivels 4 illustrated in FIG. 1 may not be required in all situations. For example, only the swivel 4 immediately adjacent to the nasal vestibular airway 2 might be provided, with a suitably bent tubing piece forming the complete angle extending toward the back of the patient's head. Furthermore, the precise nature of the swivel discussed above is one preferred embodiment, but other types of swivels may be suitable.

Figure 11:
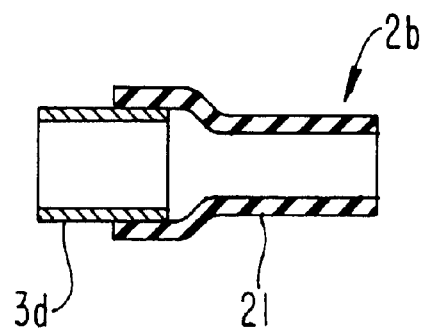
FIG. 11 is a cross-sectional view of a nasal airway of a third embodiment of the present invention.

The nasal airway has been discussed above as comprising a nasal vestibular portion 11 and 11*a*, respectively. However, the nasal airway could take the form illustrated in FIG. 11. In this figure, a naso-pharyngeal tube 21 is connected to a cylindrical adaptor tube 3*d*. A naso-pharyngeal tube 21 would be inserted into the patient's nasal passage while the adapter tubing 3*d* could be connected to other tubing or to a first swivel 4 with a compression fit.

Accordingly, the present invention provides a gas delivery apparatus that is particularly appropriate for the delivery of anesthesia to patients during plastic surgery. The apparatus takes up minimal space, and can be moved from one side of the patients head to the other side. In addition, with additional swivels 4, the apparatus may be moved from an upper position to a lower position along the patients head. Thus, many different areas of the patients head can be left unencumbered.

Furthermore, the present invention can be used in other situations, such as in the treatment of OSA. The present invention may employ the Y-connector 12*a* to connect two nasal vestibular airways for application to both nostrils. Alternatively, the primary tubing 3 might only be connected to one nostril, with the other nostril plug. Further, the nasal vestibular airway can be used together with oxygen tubing to provide a more advantageous supply of oxygen to a patient.

The elongated and rounded superior pole of the nasal vestibular airway allows stretching of the spacious apex of the vestibule of the nose to generate an elasticity that firmly holds the sharp inferior edge in the shallow space of the vestibule behind the narrow inferior nostril rim. The 45 degree wedge of the inferior pole allows the nasal vestibular airway to snugly slide over the inferior nostril rim. The acute-angle lower edge of the inferior pole allows the nasal vestibular airway to grip the narrow inner surface of the inferior nostril rim.

Further, the device according to the present invention can be tolerated without anesthesia or sedation. It is less likely to cause claustrophobia. Further, while existing devices are cumbersome and surround the face and head with a mask and straps, and a bag, the nasal vestibular airway can be paired and worn like eyeglasses with hooks or straps over the ears.

Furthermore, the nasal vestibular airway according to the present invention may be applied to deeply sedated patients in dental surgery. The device of the present application may even be considered for use in veterinary medicine, where there is no satisfactory means of assisting a spontaneously breathing but respiratory-compromised animal.

The above embodiments of the present invention have been described with respect to specific features thereof However, it is noted that the scope of the present invention is defined in the following claims, and should not be limited by the specific embodiments described above.

What is claimed is:

1. An anesthesia delivery apparatus for delivering anesthetic from an anesthesia circuit to a patient and for preventing obstruction of the patient's airway, said anesthetic delivery apparatus comprising:
   a tubing section having a first end and a second end, wherein said first end of said tubing section is to be connected to the anesthesia circuit;
   a Y portion connected to said second end of said tubing section; and
   two nasal vestibular portions connected to said Y portion, said nasal vestibular portions being operable to release the anesthetic to the patient's airway;
   said nasal vestibule portions comprising an elongated and angled wedge shaped adapted to be retained within a nasal vestibule of the patient and made of a material having sufficient hardness and inflexibility to provide a sealing force against the patient's nostril rim sufficient to allow airway pressure buildup to prevent obstruction of the patient's airway while under sedation.

2. An anesthesia delivery apparatus according to claim 1, wherein said nasal vestibular portions each comprise a superior pole for engaging an apex of a nasal vestibule, and an inferior pole for engaging an inferior nostril rim of the nasal vestibule.

3. An anesthesia delivery apparatus according to claim 2, wherein said superior pole is elongate and rounded, and said inferior pole includes the angled wedge shaped lower end.

4. An anesthetic delivery method for delivery of an anesthetic to an airway of a patient having a nasal vestibule and for use with an anesthetic delivery apparatus comprising an anesthetic source that provides the anesthetic and a nasal vestibular portion arranged so as to receive the anesthetic from the anesthetic source, the nasal vestibular portion being capable of releasing the anesthetic, said method comprising:
   inserting the nasal vestibular portion into the nasal vestibule;
   forming a seal between the nasal vestibular portion and a surface of the nasal vestibule; and
   providing an amount of anesthetic sufficient to sedate the patient into the nasal vestibule via the nasal vestibular portion,
   wherein the seal promotes airway pressure buildup that is sufficient to prevent obstruction of the airway while under sedation and prevents leakage of the anesthetic to outside of the nasal vestibule.

5. An anesthetic delivery method for delivery of an anesthetic to an airway of a patient having a nasal vestibule and for use with an anesthetic delivery apparatus comprising an anesthetic source that provides the anesthetic and a nasal vestibular portion having a shape such that the nasal vestibular portion provides an outward force on an inner surface of the nasal vestibule, due to elasticity of the nasal vestibule, for retaining the nasal vestibular portion in the nasal vestibule, the nasal vestibular portion being arranged so as to receive the anesthetic from the anesthetic source, the nasal vestibular portion being capable of releasing the anesthetic, said method comprising:
   inserting the nasal vestibular portion into the nasal vestibule thereby forming a seal between the nasal vestibular portion and a surface of the nasal vestibule, and
   providing an amount of anesthetic sufficient to sedate the patient into the nasal vestibule via the nasal vestibular portion,
   wherein the seal promotes airway pressure buildup that is sufficient to prevent obstruction of the airway while under sedation and prevents leakage of the anesthetic to outside of the nasal vestibule.

* * * * *